US00PP18609P2

(12) United States Plant Patent
Oudshoorn

(10) Patent No.: US PP18,609 P2
(45) Date of Patent: Mar. 18, 2008

(54) *PAPAVER* PLANT NAMED 'RUFFLED PATTY'

(50) Latin Name: *Papaver orientale*
Varietal Denomination: Ruffled Patty

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/527,815

(22) Filed: Sep. 27, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP17,348 P2 * 1/2007 Oudshoorn ..... Plt./263
PP17,573 P2 * 4/2007 Oudshoorn ..... Plt./263

OTHER PUBLICATIONS

UPOV ROM GTITM Computer Database, GTI Jouve Retrieval Software 2007/02 Citation for 'Ruffled Patty'.*

* cited by examiner

*Primary Examiner*—Wendy Haas
(74) *Attorney, Agent, or Firm*—C. A. Whealy

(57) ABSTRACT

A new and distinct cultivar of *Papaver* plant named 'Ruffled Patty', characterized by its upright plant habit; moderately vigorous growth habit; and large flowers with ruffled dark pink-colored petals.

2 Drawing Sheets

Botanical designation: *Papaver orientale.*
Cultivar denomination: 'Ruffled Patty'.

BACKGROUND OF THE INVENTION

The present invention relates to a new and distinct cultivar of *Papaver,* botanically known as *Papaver orientale* and hereinafter referred to by the name 'Ruffled Patty'.

The new *Papaver* originated from an open-pollination in 2000 of an unnamed selection of *Papaver orientale,* not patented, as the female, or seed, parent with an unknown selection of *Papaver orientale,* as the male, or pollen, parent. The new *Papaver* was discovered and selected by the Inventor as a single flowering plant from within the progeny of the stated open-pollination grown in a controlled environment in Rijpwetering Wetering, The Netherlands in 2005.

Asexual reproduction of the new cultivar by divisions in Rijpwetering, The Netherlands has shown that the unique features of this new *Papaver* are stable and reproduced true to type in successive generations.

SUMMARY OF THE INVENTION

Plants of the cultivar Ruffled Patty have not been observed under all possible environmental conditions. The phenotype may vary somewhat with variations in environment such as temperature and light intensity without, however, any variance in genotype.

The following traits have been repeatedly observed and are determined to be the unique characteristics of 'Ruffled Patty'. These characteristics in combination distinguish 'Ruffled Patty' as a new and distinct cultivar of *Papaver:*

1. Upright plant habit.
2. Moderately vigorous growth habit.
3. Large flowers with ruffled dark pink-colored petals.

Plants of the cultivar Ruffled Patty differ from plants of the parent selections and other *Papaver* cultivars known to the Inventor in plant height as plants of the new *Papaver* are more compact than plants of the parent selections and other cultivars known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Papaver.*

The photograph on the first sheet is a side perspective view of typical plants of 'Ruffled Patty' grown in an outdoor nursery.

The photograph at the top of the second sheet is a close-up view of a typical flower of 'Ruffled Patty'.

The photograph at the bottom of the second sheet is a close-up view of a typical leaf of 'Ruffled Patty'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late spring/early summer in an outdoor nursery in Rijpwetering, The Netherlands for about one year. During the production of the plants, day temperatures ranged from 14° C. to 27° C. and night temperatures ranged from 5° C. to 14° C.

Botanical classification: *Papaver orientale* cultivar Ruffled Patty.

Parentage:

*Female parent.*—Unnamed selection of *Papaver orientale,* not patented.

*Male parent.*—Unknown selection of *Papaver orientale,* not patented.

Propagation:

*Type.*—By divisions.

*Root description.*—Thick, fleshy; light brown in color.

Plant description:

*Form.*—Herbaceous perennial flowering plant; mostly upright; columnar. Basally branching, rosette; flowering stems arise from the base. Moderately vigorous growth habit.

*1. Plant height.*—About 98 cm.

*Plant width.*—About 84 cm.

*Branch description.*—Arrangement: Basal branching; about five basal branches develop per plant. Length: About 87 cm. Diameter: About 9 mm. Internode length: About 18.3 cm. Strength: Strong. Aspect: Upright. Texture: Pubescent; rough. Color: 144A.

Foliage description:

*Arrangement.*—Alternate, simple.

*Length.*—About 47.3 cm.

*Width.*—About 21.2 cm.

*Shape.*—Pinnatifid to pinnatisect.

*Apex.*—Acute.

*Base.*—Cuneate.

*Margin.*—Serrate or doubly serrate.

*Texture, upper and lower surfaces.*—Pubescent; rough.

*Venation pattern.*—Pinnate.

*Color.*—Developing foliage, upper and lower surfaces: 143A. Fully expanded foliage, upper surface: 143A; venation, 143A. Fully expanded foliage, lower surface: 138B; venation, 138D.

*Petiole length.*—About 12.4 cm.

*Petiole diameter.*—About 9 mm.

*Petiole color, upper and lower surfaces.*—144A to 144B.

Flower description:

*Flower arrangement and appearance.*—Large semi-double rotate flowers; flowers terminal and face mostly upright; about five flowers per plant at one time.

*Natural flowering season.*—Continuous flowering from mid-May to late June in The Netherlands.

*Flower longevity on the plant.*—About three days; flowers not persistent.

*Fragrance.*—None detected.

*Flower buds.*—Length: About 5.9 cm. Diameter: About 4.6 cm. Shape: Broadly ovate. Texture: Densely pubescent. Color: 143A.

*Flower diameter.*—About 23.4 cm.

*Flower depth (height).*—About 10.8 cm.

*Petals.*—Arrangement: About six in two whorls. Length: About 11.5 cm. Width: About 14.7 cm. Shape: Roughly reniform. Apex: Irregular, deeply incised; ruffled in appearance. Margin: Irregular, deeply incised; undulate; ruffled in appearance. Texture, upper and lower surfaces: Smooth, glabrous. Color: When opening and fully opened, upper surface: 185D to slightly lighter than 185D; towards the apex, 186D; towards the base, 187B; irregular basal black spot, 202A. When opening and fully opened, lower surface: 185D; towards the base, 187B; venation at site of upper surface basal black spot, 202A.

*Sepals.*—Arrangement: About four in a single whorl. Length: About 3.8 cm. Width: About 3.2 cm. Shape: Pinnatisect. Apex: Acute. Margin: Serrate. Texture, upper and lower surfaces: Densely pubescent. Color, upper surface: 141A to 141B. Color, lower surface: 137A.

*Peduncles.*—Length: About 87 cm. Diameter: About 9 mm. Strength: Strong. Texture: Pubescent; rough. Color: 144A.

*Reproductive organs.*—Stamens: Quantity per flower: About 300. Filament length: About 1.8 cm. Filament color: 202A; towards the base, 187A. Anther shape: Narrowly oblong. Anther length: About 4 mm. Anther color: 202A. Pollen amount: Scarce. Pollen color: N186A to 202A. Pistils: Quantity per flower: About twelve. Pistil length: About 8 mm. Stigma shape: Narrowly oblong. Stigma color: N186A to N186B and 184B. Ovary color: 144B to 144D.

*Fruits.*—Type: Capsule. Quantity per flower: One. Length: About 2.3 cm. Diameter: About 3 cm. Color: 136A to 137A.

*Seeds.*—Quantity per fruit: About 900. Length: About 1 mm. Diameter: About 1 mm. Color: 202A to 202B.

Disease/pest resistance: Plants of the new *Papaver* have not been noted to be resistant to pathogens and pests common to *Papaver.*

Garden performance: Plants of the new *Papaver* have exhibited good tolerance to rain, wind, high temperatures of 30° C. and are hardy to USDA Zone 4.

It is claimed:

1. A new and distinct *Papaver* plant named 'Ruffled Patty' as illustrated and described.

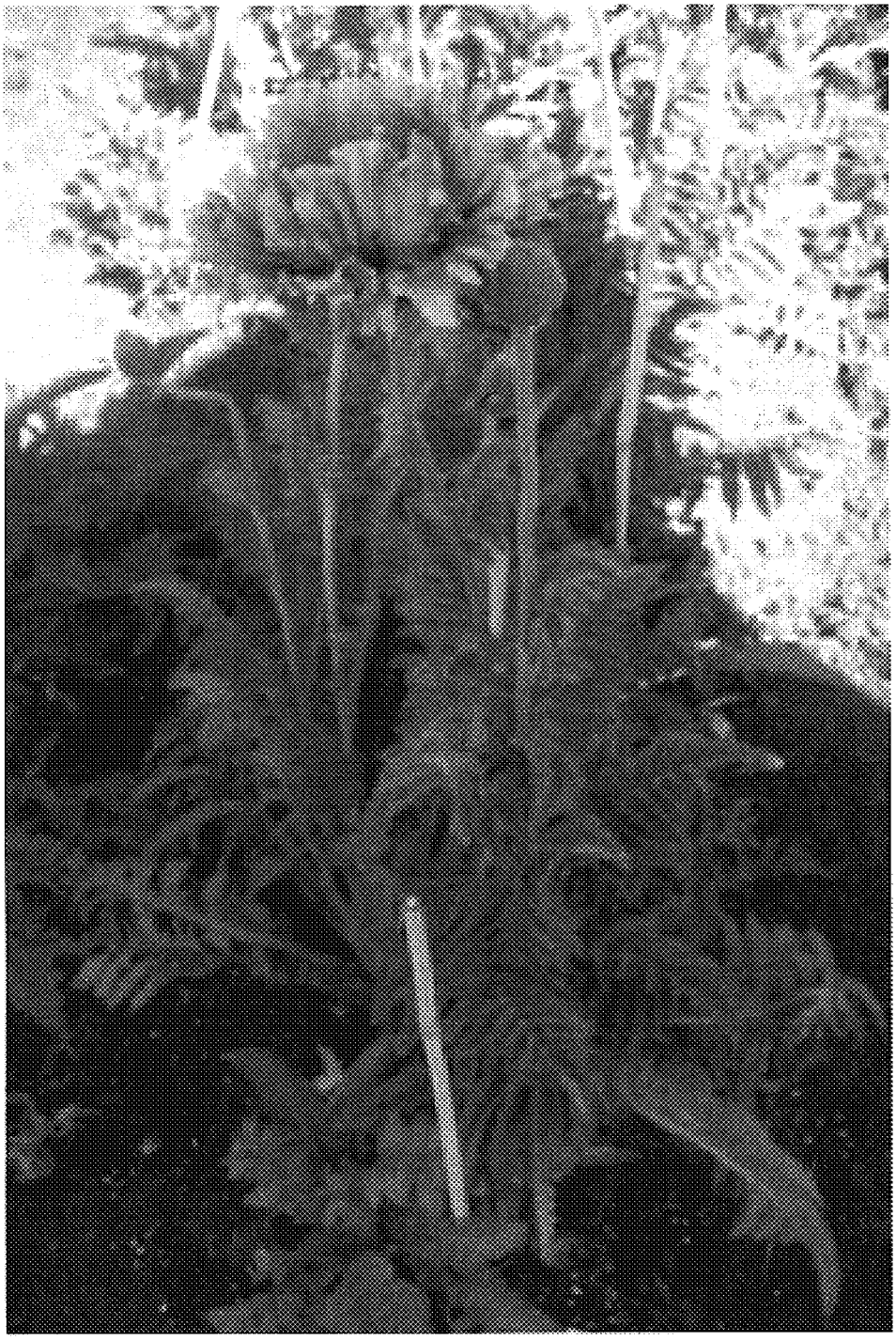

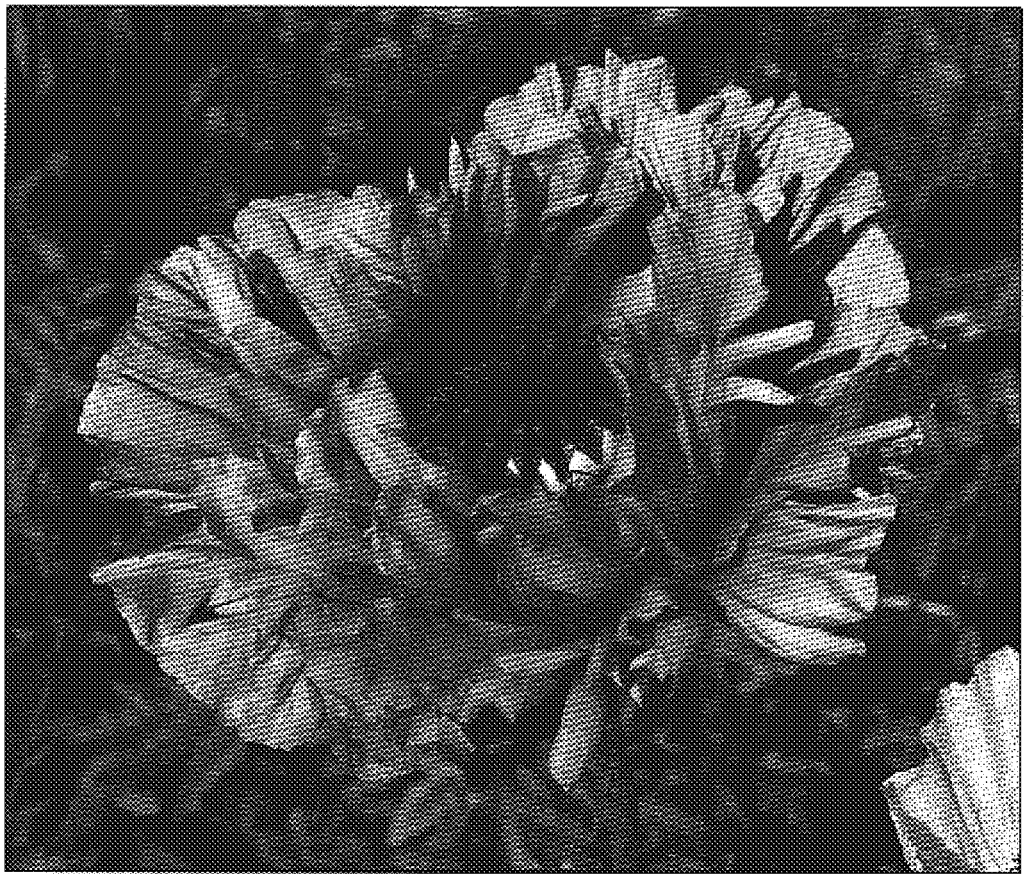
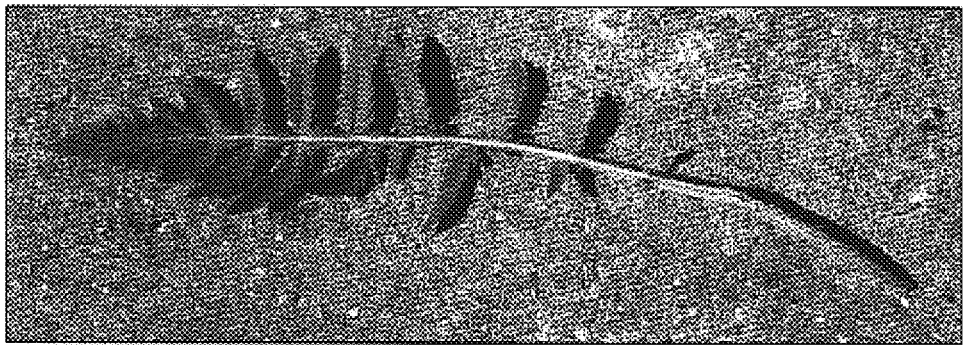

* * * * *